United States Patent
Eggenweiler et al.

(10) Patent No.: US 6,737,436 B1
(45) Date of Patent: May 18, 2004

(54) PYRROLE DERIVATIVES AS PHOSPHODIESTERASE VII INHIBITORS

(75) Inventors: Hans-Michael Eggenweiler, Weiterstadt (DE); Rochus Jonas, Darmstadt (DE); Michael Wolf, Darmstadt (DE); Michael Gassen, Griesheim (DE); Thomas Welge, Alsbach (DE)

(73) Assignee: Merck Patent GmbH, Darmstadt (DE)

( * ) Notice: Subject to any disclaimer, the term of this patent is extended or adjusted under 35 U.S.C. 154(b) by 9 days.

(21) Appl. No.: 10/129,261

(22) PCT Filed: Oct. 25, 2000

(86) PCT No.: PCT/EP00/10526
§ 371 (c)(1),
(2), (4) Date: May 3, 2002

(87) PCT Pub. No.: WO01/32618
PCT Pub. Date: May 10, 2001

(30) Foreign Application Priority Data

Nov. 4, 1999 (DE) .......................... 199 53 025

(51) Int. Cl.⁷ .................... A61K 31/402; C07D 207/36
(52) U.S. Cl. .................. 514/423; 548/532; 558/395
(58) Field of Search .............. 548/532; 514/423

(56) References Cited

FOREIGN PATENT DOCUMENTS

DE        154827        4/1982
WO        9825896       6/1998

OTHER PUBLICATIONS

Abdelhamid et al. Heterocycles, vol. 24, No. 1, 1986, pp. 101–107.*
Abdelhamid et al. Heterocycles, vol. 27, No. 8, 1988, pp. 1861–1866.*
Schafer et al. J. Prakt. Chem. 334(1992) 491–496.*
Abdel–Ghany et al. Synthetic Communications, 25(8), 1119–1131 (1995).*
Gewaki K., et al., "Synthesis of 3–aminopyrroles by Thorpe–Ziegler cyclization," Journal; Fur Praktische Chemie, Chemiker Zeitung., Bd. 334, Nr. 6, 1992, 491–496, XP000973575, Wiley VCH, Weinheim., DE.

Abdelhamid A. O., et al., Reactions with Heterocyclic Enaminonitriles. Synthesis of pyrrolo'2,3–bipyridine, pyrrolo'2,3–dipyrimidine and pyrrole derivatives: Heterocycles., Bd. 27, Nr. 8, 1988, 1861–1866, XP000973572 Elsevier Science Publishers B.V. Amsterdam., NL.

Datebase Chemcats 'Online/ Chemical Abstracts Service, Columbus, Ohio, AN 1998:586408, Apr. 3, 2000.

* cited by examiner

Primary Examiner—Ceila Chang
Assistant Examiner—Rebecca Anderson
(74) Attorney, Agent, or Firm—Millen, White, Zelano & Branigan, P.C.

(57) ABSTRACT

Compounds of the formula I

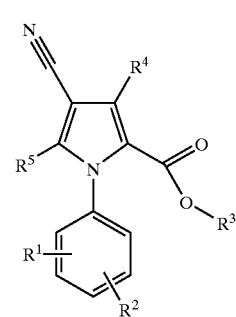

in which $R^1$ and $R^2$, independently of one another, each denote H, A, OA, SA or Hal, $R^3$ denotes H or A, $R^4$ denotes A or $NH_2$, $R^5$ denotes H, $NH_2$, NHA or $NA_2$, A denotes alkyl having 1 to 10 carbon atoms, alkenyl, cycloalkyl or alkylenecycloalkyl, Hal denotes F, Cl, Br or I, and their physiologically acceptable salts and/or solvates, as phosphodiesterase VII inhibitors.

13 Claims, No Drawings

PYRROLE DERIVATIVES AS PHOSPHODIESTERASE VII INHIBITORS

The invention relates to compounds of the formula I

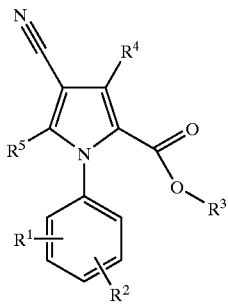

in which
- $R^1$ and $R^2$, independently of one another, each denote H, A, OA, SA or Hal,
- $R^3$ denotes H or A,
- $R^4$ denotes A or $NH_2$,
- $R^5$ denotes H, $NH_2$, NHA or $NA_2$,
- A denotes alkyl having 1 to 10 carbon atoms, alkenyl, cycloalkyl or alkylenecycloalkyl,
- Hal denotes F, Cl, Br or I, and their physiologically acceptable salts and/or solvates, as phosphodiesterase VII inhibitors.

The invention furthermore relates to the use of the compounds of the formula I for the preparation of a medicament for combating allergic diseases, asthma, chronic bronchitis, atopical dermatitis, psoriasis and other skin diseases, inflammatory diseases, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS.

Pyrrole derivatives of the formula I have been described, for example, by K. Gewald et al. in J. Prakt. Chem./Chem.-Ztg. (1992), 334 (6), 491–496.

The invention had the object of finding novel compounds having valuable properties, in particular those which can be used for the production of medicaments.

It has been found that the compounds of the formula I and their salts have very valuable pharmacological properties and are well tolerated.

In particular, they exhibit specific inhibition of "Rolipram insensitive" cAMP phosphodiesterase (PDE VII).

The biological activity of the compounds of the formula I can be determined by methods as described, for example, by M. A. Giembycz et al. in Br. J. Pharmacol. (1996), 118, 1945–1958.

The affinity of the compounds for cAMP phosphodiesterase (PDE VII) is determined by measuring their $IC_{50}$ values (concentration of the inhibitor that is required to achieve 50% inhibition of the enzyme activity). In order to carry out the determinations, homogenized SK-N-SH neuroblastoma cells were used instead of T-lymphocytes, and PDE III inhibition was carried out using CI-930. This is a selective PDE III inhibitor (J. A. Bristol et al., J. Med. Chem. 1984, 27(9), 1099–1101).

Alternatively, SK-N-SH is replaced by HUT-78 and instead of using CI-930 inhibition is carried out with trequensin (D. Ruppert et al., Life Sci. 31:2037, 1982).

The compounds of the formula I can be employed for the treatment of asthmatic illnesses.

The anti-asthmatic action can be determined, for example, analogously to the method of T. Olsson, Acta allergologica 26, 438–447 (1971).

Since cAMP inhibits osteoclastic cells and stimulates osteogenetic cells (S. Kasugai et al., M 681, and K. Miyamoto, M 682, in Abstracts of the American Society for Bone and Mineral Research, 18th Annual Meeting, 1996), the compounds of the formula I can be employed for the treatment of osteoporosis.

The compounds also exhibit an antagonistic action to the production of $TNF_\alpha$ (tumour necrosis factor) and are therefore suitable for the treatment of allergic and inflammatory diseases, autoimmune diseases, such as, for example, rheumatoid arthritis, multiple sclerosis, Crohn's disease, diabetes mellitus or ulcerative colitis, transplant rejection reactions, cachexia and sepsis.

The anti-inflammatory action of the substances of the formula I and their effectiveness for the treatment of, for example, autoimmune diseases such as multiple sclerosis or rheumatoid arthritis can be determined analogously to the methods of N. Sommer et al., Nature Medicine 1, 244–248 (1995), or L. Sekut et al., Clin. Exp. Immunol. 100, 126–132 (1995).

The compounds can be employed for the treatment of cachexia. The anti-cachectic action can be tested in TNF-dependent models of cachexia (P. Costelli et al., J. Clin. Invest. 95, 2367 ff. (1995); J. M. Argiles et al., Med. Res. Rev. 17, 477 ff. (1997)).

The PDE VII inhibitors can also inhibit the growth of tumour cells and are therefore suitable for tumour therapy (for PDE IV inhibitors, cf. D. Marko et al., Cell Biochem. Biophys. 28, 75 ff. (1998)).

They can furthermore be employed for the therapy of sepsis and for the treatment of memory disorders, atherosclerosis, atopical dermatitis and AIDS, furthermore for the treatment of T cell-dependent diseases (L. Li et al., Science, 1999, 283, 848–851).

The compounds of the formula I can be employed as medicament active ingredients for PDE VII inhibition in human and veterinary medicine.

A denotes alkyl having 1–10 carbon atoms and has 1, 2, 3, 4, 5, 6, 7, 8, 9 or 10 carbon atoms and preferably denotes methyl, ethyl or propyl, furthermore preferably isopropyl, butyl, isobutyl, sec-butyl or tert-butyl, but also n-pentyl, neopentyl, isopentyl or hexyl. In these radicals, 1–7 H atoms may also be replaced by F and/or Cl. A therefore also denotes, for example, trifluoromethyl or pentafluoroethyl.

A also denotes cycloalkyl having 3–8 carbon atoms and preferably denotes, for example, cyclopentyl or cyclohexyl.

A also denotes alkenyl. Alkenyl has 2–10 carbon atoms, is linear or branched and denotes, for example, vinyl, propenyl or butenyl. A furthermore denotes alkylenecycloalkyl. Alkylenecycloalkyl has 4–10 carbon atoms and preferably denotes, for example, methylenecyclopentyl, ethylenecyclopentyl, methylenecyclohexyl or ethylenecyclohexyl.

$R^1$ and $R^2$ preferably each denote, independently of one another, H, methyl, ethyl, propyl, butyl, isopropyl, tert-butyl, methoxy, ethoxy, propoxy, isopropoxy, butoxy, S-methyl, S-ethyl, F or Cl.

$R^3$ preferably denotes H, methyl or ethyl.

$R^4$ preferably denotes methyl, ethyl, propyl, butyl or $NH_2$.

$R^5$ preferably denotes H, amino, methylamino, ethylamino, dimethylamino or diethylamino.

A base of the formula I can be converted into the associated acid-addition salt using an acid, for example by reaction of equivalent amounts of the base and the acid in a suitable solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethane-sulfonic acid, benzenesulfonic acid, p-toluenesulfonic acid, naphthalene-mono- and -disulfonic acids, laurylsulfuric acid. Salts with physiologically unacceptable acids, for example picrates, can be used for the isolation and/or purification of the compounds of the formula I.

The invention furthermore relates to pharmaceutical preparations comprising at least one phosphodiesterase VII inhibitor of the formula I and/or one of its physiologically acceptable salts and/or solvates for combating allergic diseases, asthma, chronic bronchitis, atopical dermatitis, psoriasis and other skin diseases, inflammatory diseases, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS.

The substances here are generally preferably administered in doses of between about 1 and 500 mg, in particular between 5 and 100 mg, per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the rate of excretion, medicament combination and severity of the particular disease to which the therapy applies. Oral administration is preferred.

The pharmaceutical preparations can be used as medicaments in human or veterinary medicine. Suitable excipients are organic or inorganic substances which are suitable for enteral (for example oral), parenteral or topical administration and with which the novel compounds do not react, for example water, vegetable oils, benzyl alcohols, alkylene glycols, polyethylene glycols, glycerol triacetate, gelatine, carbohydrates, such as lactose or starch, magnesium stearate, talc, Vaseline. Suitable for oral administration are, in particular, tablets, pills, coated tablets, capsules, powders, granules, syrups, juices or drops, suitable for rectal administration are suppositories, suitable for parenteral administration are solutions, preferably oily or aqueous solutions, furthermore suspensions, emulsions or implants, and suitable for topical application are ointments, creams or powders. The novel compounds may also be lyophilized and the resultant lyophilizates used, for example, for the preparation of injection preparations. The preparations indicated may be sterilized and/or comprise auxiliaries, such as lubricants, preservatives, stabilizers and/or wetting agents, emulsifiers, salts for modifying the osmotic pressure, buffer substances, dyes, flavours and/or a plurality of further active ingredients, for example one or more vitamins.

The invention relates, in particular, to the compounds of the formula I listed in the examples below and their physiologically acceptable salts and/or solvates as PDE VII inhibitors and to their use for the preparation of a medicament for combating allergic diseases, asthma, chronic bronchitis, atopical dermatitis, psoriasis and other skin diseases, inflammatory diseases, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS.

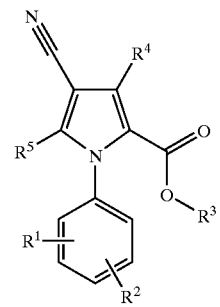

| Example | $R^1$ | $R^2$ | $R^3$ | $R^4$ | $R^5$ |
|---|---|---|---|---|---|
| 1 | H | H | H | Me | H |
| 2 | 4-Cl | H | Et | Amino | H |
| 3 | H | H | Et | Me | Amino |
| 4 | H | H | Et | Amino | H |
| 5 | H | H | Et | H | Amino |
| 6 | 3-Cl | 4-OMe | Et | Amino | H |
| 7 | 3-Cl | 4-OMe | Et | Me | Amino |
| 8 | 4-OCF$_3$ | H | Et | Amino | H |

Me = methyl;
Et = ethyl

The examples below relate to pharmaceutical preparations:

EXAMPLE A

Injection Vials

A solution of 100 g of a phosphodiesterase VII inhibitor of the formula I and 5 g of disodium hydrogenphosphate in 3 l of bidistilled water is adjusted to pH 6.5 using 2N hydrochloric acid, sterile filtered, transferred into injection vials, lyophilized under sterile conditions and sealed under sterile conditions. Each injection vial contains 5 mg of active ingredient.

EXAMPLE B

Suppositories

A mixture of 20 g of a phosphodiesterase VII inhibitor of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of a phosphodiesterase VII inhibitor of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilized by irradiation. This solution can be used in the form of eye drops.

EXAMPLE D

Ointment 500 mg of a phosphodiesterase VII inhibitor of the formula I are mixed with 99.5 g of Vaseline under aseptic conditions.

EXAMPLE E

Tablets

A mixture of 1 kg of phosphodiesterase VII inhibitor of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of phosphodiesterase VII inhibitor of the formula I are introduced into hard gelatine capsules in a conventional manner in such a way that each capsule contains 20 mg of the active ingredient.

EXAMPLE H

Ampoules

A solution of 1 kg of phosphodiesterase VII inhibitor of the formula I in 60 l of bidistilled water is sterile filtered, transferred into ampoules, lyophilized under sterile conditions and sealed under sterile conditions. Each ampoule contains 10 mg of active ingredient.

EXAMPLE I

Inhalation Spray 14 g of phosphodiesterase VII inhibitor of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

What is claimed is:
1. A compound of formula I

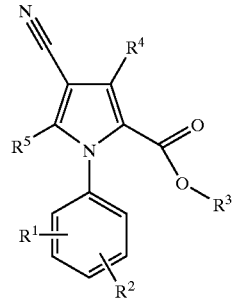

in which
R$^1$ and R$^2$, independently of one another, is H, A, OA, SA or Hal,
R$^3$ is H or A,
R$^4$ is A or NH$_2$,
R$^5$ is H, NH$_2$, NHA or NA$_2$,
A is alkyl having 1 to 10 carbon atoms, alkenyl, cycloalkyl or alkylenecycloalkyl,
Hal denotes F, Cl, Br or I,
or a physiologically acceptable salt or solvate thereof, wherein R$^1$ and R$^2$ are not both H and wherein when one of R$^1$ or R$^2$ is H, the other cannot be CH$_3$, OCH$_3$ or Cl.

2. A pharmaceutical composition comprising a therapeutically effective amount of at least one compound of formula I

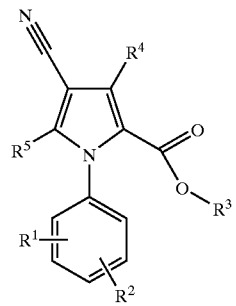

in which
R$^1$ and R$^2$, independently of one another, is H, A, OA, SA or Hal,
R$^3$ is H or A,
R$^4$ is A or NH$_2$,
R$^5$ is H, NH$_2$, NHA or NA$_2$,
A is alkyl having 1 to 10 carbon atoms, alkenyl, cycloalkyl or alkylenecycloalkyl,
Hal denotes F, Cl, Br or I, or a physiologically acceptable salt or solvate thereof, and a pharmaceutically acceptable excipient.

3. The pharmaceutical composition of claim 2, wherein R$^1$, R$^2$, R$^3$ and R$^5$ are H and R$^4$ is methyl.

4. The pharmaceutical composition of claim 2, wherein R$^1$ is 4-Cl, R$^2$ is H, R$^3$ is ethyl, R$^4$ is amino and R$^5$ is H.

5. The pharmaceutical composition of claim 2, wherein R$^1$ and R$^2$ are H, R$^3$ is ethyl, R$^4$ is methyl and R$^5$ is amino.

6. The pharmaceutical composition of claim 2, wherein $R^1$ and $R^2$ are H, $R^3$ is ethyl, $R^4$ is amino and $R^5$ is H.

7. The pharmaceutical composition of claim 2, wherein $R^1$ and $R^2$ are H, $R^3$ is ethyl, $R^4$ is H and $R^5$ is amino.

8. The pharmaceutical composition of claim 2, wherein $R^1$ is 3-Cl, $R^2$ is 4-O-methyl, $R^3$ is ethyl, $R^4$ is amino and $R^5$ is H.

9. The pharmaceutical composition of claim 2, wherein $R^1$ is 3-Cl, $R^2$ is 4-O-methyl, $R^3$ is ethyl, $R^4$ is methyl and $R^5$ is amino.

10. The pharmaceutical composition of claim 2, wherein $R^1$ is 4-OCF$_3$, $R^2$ is H, $R^3$ is ethyl, $R^4$ is amino and $R^5$ is H.

11. The compound of claim 1, wherein $R^1$ is 3-Cl, $R^2$ is 4-O-methyl, $R^3$ is ethyl, $R^4$ is amino and $R^5$ is H.

12. The compound of claim 1, wherein $R^1$ is 3-Cl, $R^2$ is 4-O-methyl, $R^3$ is ethyl, $R^4$ is methyl and $R^5$ is amino.

13. The compound of claim 1, wherein $R^1$ is 4-OCF$_3$, $R^2$ is H, $R^3$ is ethyl, and $R^4$ is amino and $R^5$ is H.

\* \* \* \* \*